US008314215B2

(12) United States Patent
Bogyo et al.

(10) Patent No.: US 8,314,215 B2
(45) Date of Patent: Nov. 20, 2012

(54) MILD CHEMICALLY CLEAVABLE LINKER SYSTEM

(75) Inventors: Matthew S. Bogyo, Redwood City, CA (US); Steven H. L. Verhelst, Palo Alto, CA (US); Marko Fonovic, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 601 days.

(21) Appl. No.: 12/376,053

(22) PCT Filed: Aug. 1, 2007

(86) PCT No.: PCT/US2007/017233
§ 371 (c)(1),
(2), (4) Date: Mar. 26, 2009

(87) PCT Pub. No.: WO2008/094205
PCT Pub. Date: Aug. 7, 2008

(65) Prior Publication Data
US 2010/0003735 A1 Jan. 7, 2010

Related U.S. Application Data

(60) Provisional application No. 60/835,548, filed on Aug. 4, 2006.

(51) Int. Cl.
*C09B 29/03* (2006.01)
*C09B 29/12* (2006.01)
*C12N 1/00* (2006.01)
*G01N 33/00* (2006.01)

(52) U.S. Cl. ........................................ 534/657; 534/732
(58) Field of Classification Search .................... None
See application file for complete search history.

(56) References Cited

U.S. PATENT DOCUMENTS

| 4,279,998 | A | | 7/1981 | Shahani |
| 5,252,707 | A | * | 10/1993 | Ozaki et al. ................... 530/345 |
| 5,527,711 | A | * | 6/1996 | Tom-Moy et al. ............ 436/518 |
| 6,602,987 | B1 | * | 8/2003 | Wilchek et al. ............. 530/391.3 |
| 6,818,420 | B2 | | 11/2004 | Chou et al. |
| 6,951,682 | B1 | | 10/2005 | Zebala |
| 2002/0076739 | A1 | | 6/2002 | Aebersold et al. |
| 2004/0038319 | A1 | | 2/2004 | Aebersold et al. |
| 2004/0146516 | A1 | | 7/2004 | Roben et al. |
| 2005/0010059 | A1 | | 1/2005 | Beauchamp et al. |
| 2005/0233399 | A1 | | 10/2005 | Aebersold et al. |
| 2006/0147985 | A1 | | 7/2006 | Barone et al. |
| 2006/0154325 | A1 | | 7/2006 | Bogyo et al. |
| 2007/0036725 | A1 | * | 2/2007 | Bogyo et al. ................... 424/9.6 |
| 2009/0252677 | A1 | * | 10/2009 | Bogyo et al. ................. 424/1.65 |
| 2010/0068150 | A1 | * | 3/2010 | Bogyo et al. ................... 424/9.6 |

FOREIGN PATENT DOCUMENTS
WO 2008094205 A2 8/2008

OTHER PUBLICATIONS

Satishkumar B.C., et al., "Reversible Fluoresence Quenching in Carbon Nanotubes for Bomolecular Sensing", Nature Nanotechnology, 2, Sep. 2007.*
Kemp et al., "Ehrlich chromogens, probable cross-links in elastin and collagen," Biochem. J. (1988) 252, 387-393.
Denny et al., "125I labeled crosslinking reagent that is hydrophilic, potoactivatable, and cleavable through an azo linker," Proc. Nat. Acad. Sci., 1984, 81:5286-5294.
Greenbaum, et al., Epoxide electrophiles as activity-dependent cysteine protease profiling and discovery tools, Chemistry & Biology, 2000, vol. 7, No. 8, 569-581.
Tessenshohn, et al., Japan's novelty grace period solves the dilemma of 'publish and perish', Nature Biotechnology, Jan. 2007, vol. 25, No. 1, 55-57.
Campbell, et al., "Functional profiling of the proteome with affinity labels," Chemical Biology, 2003, 7:296-303.
Marnett, et al., "Communication between the active sites and dimer interface of a herpesvirus protease revealed by a transition-state inhibitor," PNAS, May 4, 2004, vol. 101, No. 18, 6870-6875.
Verhelst, S.H.L., Fonovic, M. and Bogyo, M., "A Mild Chemically Cleavable Linker System for Functional Proteomic Applications," 2007, Angew. Chemie., 46:1284-1286.
PCT/US07/17233, International Search Report, Sep. 2, 2008.

* cited by examiner

*Primary Examiner* — Fiona T Powers
(74) *Attorney, Agent, or Firm* — David J. Aston; Peters Verny, LLP

(57) ABSTRACT

A linker system is provided where a small molecule reactive group, e.g., an activity based probe which binds to certain enzymes at the active site, is linked through an aryl diazo linker to an affinity molecule such as biotin. The reactive group may comprise a number of functionalities known to react with a specific target to be studied. This enables the probe to be exposed to analytes, such as proteins and bind specifically to them to form a complex having an affinity molecule allowing immobilization of the bound analyte on an affinity column or other support, e.g. with streptavidin. Then, the linker is cleaved without causing removal of the affinity group or dissociation of the probe from the analyte. The linker is cleaved under mild reducing conditions, e.g., dithionite. The probe is synthesized along with the linker on a solid support.

14 Claims, 7 Drawing Sheets

MTS-I-49 a

MILD CHEMICALLY CLEAVABLE LINKER SYSTEM

CROSS-REFERENCE TO RELATED APPLICATIONS

This application claims priority from U.S. Provisional Patent Application No. 60/835,548, filed on Aug. 4, 2006, which is hereby incorporated by reference in its entirety, and further claims priority to PCT/US/2007/017233, having an international filing date of 1 Aug. 2007.

STATEMENT OF GOVERNMENTAL SUPPORT

This invention was made with Government support under contract U54 RR020843 awarded by the National Institutes of Health. The Government has certain rights in this invention.

REFERENCE TO SEQUENCE LISTING, COMPUTER PROGRAM, OR COMPACT DISK

None.

BACKGROUND OF THE INVENTION

1. Field of the Invention

The present invention relates to the field of synthesis of peptides and related compounds, using solid supports, and cleavage of such compounds through cleavage of a diazo bond, releasing at least a portion of the compound from the support.

2. Related Art

One of the primary goals for the field of proteomics is finding ways to enrich specific protein targets from complex mixtures. Generally, this is accomplished with small molecular tags that allow specific modification by the formation of a stable covalent bond with reactive groups on the target protein.[1] The proteomic probes can either be generally reactive towards free nucleophiles such as thiols (i.e., ICAT reagents)[2] or react through a specific enzymatic process with a key catalytic residue.[3] The labeled targets can then be enriched using a affinity purification methods, which mainly exploit the diffusion limited binding of biotin to (immobilized) streptavidin. Although this method allows efficient isolation of even highly dilute targets, one of the primary limitations is the need for harsh, denaturing conditions to disrupt the biotin-streptavidin interaction. The elution conditions generally result in contamination of the desired probe labeled proteins with avidin monomers, proteins that were non-selectively bound to the streptavidin, and endogenously biotinylated proteins. Therefore, the incorporation of a cleavable linker between the biotin tag and the site of attachment to the target protease will be of great value, since it allows specific elution of proteins or peptides that were labeled by a given probe. Furthermore, specific cleavage of the probe structure can be used to reduce the size of the chemical modification on the target protein leading to enhanced mass spectrometry characteristics.

Recently, a number of cleavable linkers have been reported, with a focus on applications in mass spectrometry and ICAT.[4-6] ICAT reagents consist of conjugate molecules containing an affinity tag (e.g., biotin), an isotope tag and a protein-reactive group such as an iodoacetamide for attachment to cysteine SH groups in proteins. A non-deuterated and deuterated pair of ICAT reagents are used to determine the relative levels of proteins in complex protein mixtures. However, these regents require strong acid (TFA), making cleavage of labeled proteins directly from strepavidin resin problematic.

Other Patents and Publications

US 2002/0076739 to Aebersold, et al., published Jun. 20, 2002, entitled "Rapid quantitative analysis of proteins or protein function in complex mixtures," relates to the above-mentioned ICAT method. It discloses analytical reagents and mass spectrometry-based methods that employ affinity labeled protein reactive reagents having three portions: an affinity label (A) covalently linked to a protein reactive group (PRG) through a linker group (L). Thus, the linker can be cleavable, for example, by chemical, thermal or photochemical reaction. Photocleavable groups in the linker may include the 1-(2-nitrophenyl)-ethyl group. Thermally labile linkers may, for example, be a double-stranded duplex formed from two complementary strands of nucleic acid, a strand of a nucleic acid with a complementary strand of a peptide nucleic acid, or two complementary peptide nucleic acid strands which will dissociate upon heating. Cleavable linkers also include those having disulfide bonds, acid or base labile groups, including among others, diarylmethyl or trimethylarylmethyl groups, silyl ethers, carbamates, oxyesters, thioesters, thionoesters, and α-fluorinated amides and esters.

US 2006/0147985 to Barone, et al., published Jul. 6, 2006, entitled "Methods and compositions for monitoring polymer array synthesis," discloses cleavable linkers useful in monitoring polymer synthesis in an array on a substrate, exemplified by the photocleavable group MeNPOC.

US 2005/0010059 to Beauchamp, et al., Jan. 13, 2005, entitled "Chemical reagents capable of selective attachment to and reaction with peptides and proteins," discloses crown ethers capable of selectively forming non-covalent complexes and initiating intermolecular reactions with amine-containing compounds. The disclosure includes a method of covalently attaching amino acids via carbene insertion chemistry comprising adding a compound to the amino acid, where the compound comprises at least one crown ether group and a diazo group.

U.S. Pat. No. 6,951,682 to Zebala, issued Oct. 4, 2005, entitled "Porous coatings bearing ligand arrays and use thereof," discloses photoresist compounds of the formula $>C=N_2$ in which the compounds are converted by light to $>COOH+N_2$. These compounds have a ketone group adjacent to the diazo group. As stated there, the photolytic response of phenolic photoresists reflects the photochemistry of the photosensitive diazoquinone often also referred to as a diazoketone, diazo-oxide, diazoanhydride, or quinone diazide.

U.S. Pat. No. 6,818,420 to Chou, et al, issued Nov. 16, 2004, entitled "Methods of using FET labeled oligonucleotides that include a 3'-5' exonuclease resistant quencher domain and compositions for practicing the same," discloses a dark quencher having a formula wherein one or more substituted aryl groups comprise the linkage —N=N-aryl. The substituted aryl has substituents R2 through R5 which may be independently —H, halogen, —O($CH_2)_n CH_3$, —($CH_2)_n CH_3$, —$NO_2$, $SO_3$, —N[($CH_2)_n CH_3]_2$ wherein n=0 to 5 or —CN.

U.S. Pat. No. 4,279,998 to Shahani, et al., issued Jul. 21, 1981, entitled "Regenerable insoluble support for protein immobilization," discloses an insoluble support for immobilized proteins in which the protein is connected to the support by a spacer arm containing a diazo linkage, and, when the protein is denatured, the spacer arm is broken by reducing the diazo linkage to remove the denatured protein. Activated p-(N-acetyl-L-tyrosine azo) benzamidoethyl agarose beads were prepared, comprising a linkage of -benzyl-N=N=2-hydroxy, 5-heteralkly substituted benzyl.

Kemp and Scott, "Ehrlich chromogens, probable crosslinks in elastin and collagen," Biochem. J. (1988) 252, 387-393 discloses an affinity support method, utilizing a polyacrylamide substrate to which a diazobenzene group is linked via an alkali-labile phenol ester.

Denny and Blobel, "[125]I labeled crosslinking reagent that is hydrophilic, potoactivatable, and cleavable through an azo linker," Proc. Nat. Acad. Sci. 81:5286-5294 (1984) discloses a radioactive cross linker, N-[4-(Pazido-m-[125I]iodophenylazo)benzoyl]-3-aminopropyl-N'-oxysulfosuccinimide ester, which contains an aryl-N=N-aryl structure. As a model system, the derivatized protein A-Sepharose was added to human serum to determine if radioactive label could be specifically transferred from protein A to the heavy chain of IgG following photocrosslinking and cleavage of the crosslinks with sodium dithionite.

BRIEF SUMMARY OF THE INVENTION

The following brief summary is not intended to include all features and aspects of the present invention, nor does it imply that the invention must include all features and aspects discussed in this summary.

The present invention comprises a compound for labeling and immobilizing a target protein, of the formula

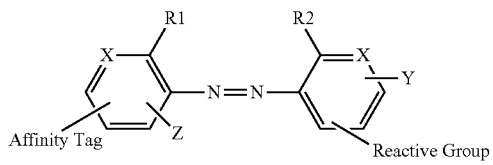

where

R1 and R2 are independently H, or hydroxyl, provided that at least one of R1 or R2 is hydroxyl;

X is independently one of C, S, N or O;

Y and Z are independently H, hydroxyl, carboxy, keto, or lower alkyl;

"Affinity Tag" represents a chemical moiety having a molecular weight of less than about 5,000 Daltons which has a specific binding partner; and "Reactive Group" represents a compound which binds to a protein at a defined site and reacts with it.

In the above formula, the bonds to Z, Y, affinity tag and reactive group may be at any available ring position including X; If R1 or R2 is H, Z or Y, respectively, may be bound at R2. The present compound is useful in "immobilizing" a target in the sense that it may contain an affinity tag that will bind to a ligand on a column, bead, microtiter plate, membrane or other solid support. In the above compound, the "Affinity Tag" may for example be selected from the group consisting of biotin, Brilliant Blue FCF (BB FCF), azorubine, phytoestrogen, digoxigenin, nickel, cobalt, zinc, and a hapten to an antibody. These materials, as described below, may bind to an immobilized ligand. For example, a hapten may be attached for binding to its cognate antibody on a column. In one aspect of the present invention, the Affinity Tag is biotin, which binds to streptavidin with high affinity.

The affinity tag may be of the formula:

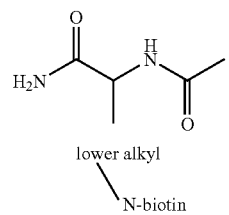

Thus, various linkers may be employed to attach affinity tags.

The compound binds to a selected target through the "Reactive Group," which may be a protease affinity label, an amine reactive group (which are known to include electrophiles such as alkyl halides or electrophiles such as an N-hydroxysuccinimide) or a thiol reactive group such as iodoacetamide or a maleimide functionality; these allow conjugation of the present compounds to the sulfhydryl group of cysteine residues. The "Reactive Group" may therefore for example be selected from the group consisting of succinimide, maleimide, iodoacetamide, carboxylic acid, mercaptoaminomonocarboxylic acids, diaminomonocarboxylic acids, monoaminodicarboxylic acids, metal chelates, semicarbazones, epoxy succinyl, acyl oxy, and peptidyl phosphonate.

These groups include those having reactive groups that form irreversible, or "suicide" enzyme inhibitors, or other specific binding properties. This is described further below.

The reactive group may further comprise a derivatized peptide that is designed to specifically recognize a particular enzyme or class of enzymes, as a pseudosubstrate. For example, in the case of protease (caspase) inhibitors, the derivatized peptide is a peptide having an AOMK group or an epoxy succinyl group, and said peptide has between 2 and 5 amino acid units.

A hydroxyl group for facilitating cleavage under mild reducing conditions, is on an aryl group and is adjacent (ortho) to the N=N (diazo) bond, on either ring. In general, the cleavable linker may be of the formula affinity tag-aryl-N=N-aryl-reactive group. As shown in FIG. 2, the affinity tag and the reactive group may be linked in the m or p positions.

A label may be bound to the reactive group, such a fluorescent label, whereby the target peptide (e.g., cysteine protease) may be not only separated, but also labeled.

Also provided is a method of preparing a composition enriched for proteins having activity to a selected probe, comprising the steps of:

(a) preparing a probe having a cleavable linkage comprising the formula: affinity tag-aryl-N=N-aryl-reactive group, wherein the reactive group reacts with a selected protein;

(b) contacting the probe with a sample comprising the protein under conditions where the probe binds to the protein;

(c) immobilizing the probe on a surface;

(d) after the probe is immobilized and the protein is bound, cleaving the cleavable linkage, while the probe remains immobilized, whereby (e) the probe-bound protein is collected from the surface into an enriched preparation.

The cleavage is carried out with a mild reducing agent; in particular a dithionite may be used without disrupting various complexes of interest.

In certain aspects, the present invention comprises a solid phase synthetic method, including the steps of:
(a) preparing a protected cleavable linker having a protective group PG, of the formula aryl-N=N-aryl-PG;
(b) attaching the compound obtained in step (a) to a solid support;
(c) attaching an affinity tag to the immobilized compound of step (b);
(d) attaching between one and five amino acids to the compound of (b) on the support;
(e) attaching to the compound of (d) a reactive group; and
(f) eluting the cleavable affinity probe of the formula affinity tag-aryl-N=N-aryl-probe from the solid support.

DETAILED DESCRIPTION OF THE PREFERRED EMBODIMENT

Overview

Described below is a novel diazobenzene derivative and its application as a chemoselective cleavable linker system (FIG. 1).

Figure 1A:
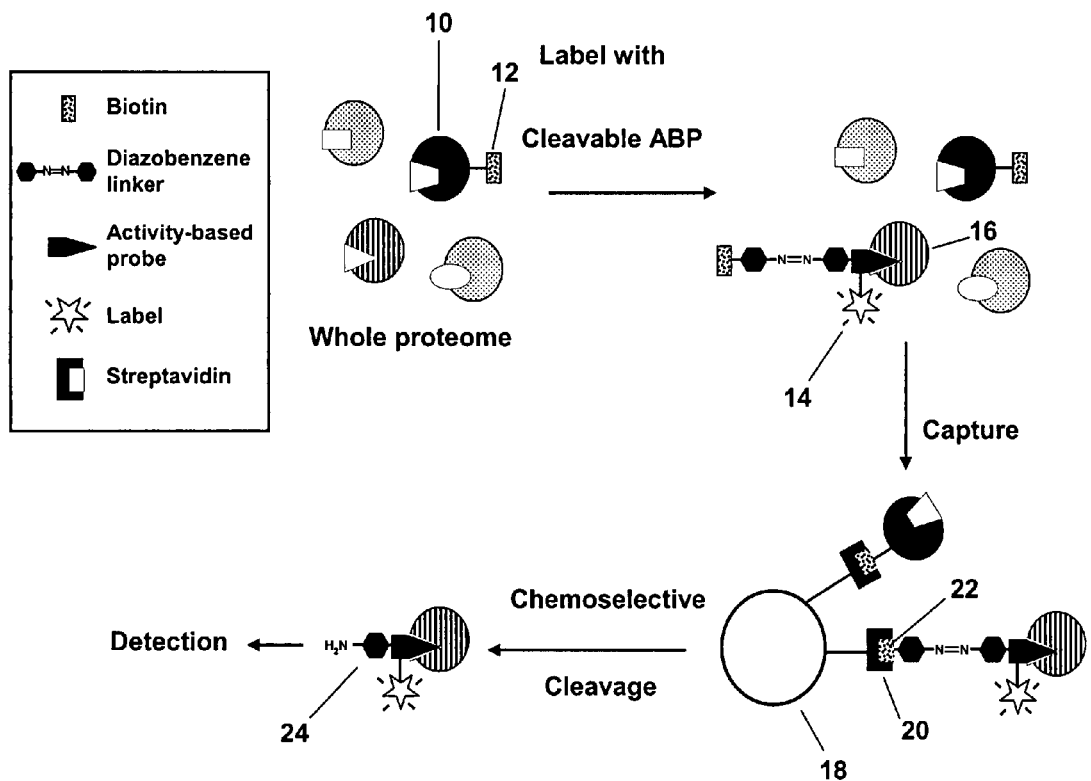
FIG. 1A is a diagram showing a general strategy of a cleavable activity-based probe. Enrichment of specifically labeled proteases is followed by a mild chemoselective cleavage, only releasing the target proteases.

FIG. 1A shows a mixture of proteins in which one protein species 10 is labeled with biotin 12. The mixture is exposed to a labeled, cleavable ABP (activity based probe). As is known in the art, an activity based probe only binds to an active protein, typically an enzyme, and does not bind to the inactive form of the protein. See, U.S. Pat. No. 6,872,574 to Cravatt, et al. Mar. 29, 2005, entitled "Proteomic analysis." The present complex is illustrated as having the formula biotin-diazobenzene linker-ABP. The ABP also contains a label, e.g., the fluorescent dye tetramethyl rhodamine (TAMRA) 14. The ABP is specific for one protein species, e.g., cathepsin 16. A complex between the enzyme to be labeled 16 and the ABP is formed. The mixture is then exposed to a solid phase 18, such as a microtiter plate, beads, etc. coated with streptavidin 20, as is known in the art. The mixture is passed over the solid phase, and the ABP, complexed to the cognate protein 16, binds through a biotin tag 22 to the solid phase 18, as does the species 10, labeled only with biotin. However, in contrast to the biotin labeled protein species 10, the ABP can be removed through chemoselective cleavage in which the —N=N— bond is cleaved, leaving a terminal amine group. The free ABP 24 can be detected by the label 14. Its presence in the protein mixture can then be quantified, and the ABP-protein complex is prepared in relatively pure form for further experiments.

Figure 1B:
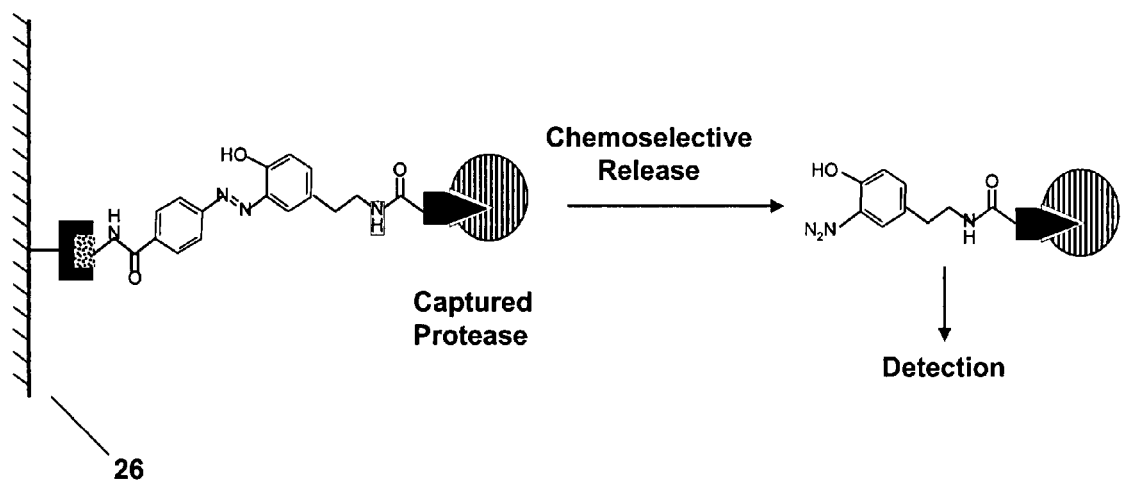
FIG. 1B shows a scheme in which the cleavable probe is immobilized and applied for the enrichment of specific protease targets from a complex proteome.

FIG. 1B shows an alternative view of the solid phase immobilization of ABP on a solid phase 26 and subsequent release through cleavage of the diazo linkage, such as by reduction.

We chose to use diazobenzenes as exemplary linkers as they can be cleaved under mild reducing conditions using sodium dithionite or tin(II) chloride. Importantly, these cleavage reaction conditions are compatible with biochemical systems, as exemplified by the use of diazobenzenes as cleavable crosslinking reagents for proteins[7] and, more recently, in the functionalization of a tyrosine residue on the surface of viral capsids.[8]

Our linker can be easily incorporated into small molecular probes that allow the isolation of specific protein targets by streptavidin affinity purification (FIG. 1). Chemoselective cleavage of the linker produces a fragment containing a free amine that should enhance ionization of labeled peptides. Preliminary mass spectrometry data show highly selective identification of target proteases with virtually no signals observed from background proteins.

Generally, the present cleavable linker system comprises (1) an affinity tag attached to (2) a diazo-aryl cleavable linker, which in turn is attached to (3) a reactive group, which, e.g., may be an ABP, as illustrated above, or other analyte labeling probe (where, typically, the "analyte" is a protein in a complex mixture), such as an ICAT reagent, etc. Components (1) and (3) are therefore separated upon cleavage of the linker (2), releasing the probe and the attached peptide. The components are chosen so that the cleavage of the linker is brought about without separating the probe from its cognate peptide. An enriched preparation of the peptide is thus obtained, with the attached probe. The probe may be further labeled e.g., with TAMRA and, therefore the present methods may give rise to a purified preparation of labeled analyte.

The present cleavage system may be adapted for use with ICAT for mass spectrometric analysis of proteins. In this technique, as described in US 2005/0049406 to Lerchen, Hans-Georg, et al., affinity tags which have been isotope-coded differentially and tandem mass spectrometry are used. This method can be enlisted for quantitatively analyzing complex protein mixtures ((a) S. P. Gygi et al., Nature Biotechnology, 1999, 17, 994; (b) R. H. Aebersold et al., WO 00/11208). Pairs or groups of peptides which are labeled with affinity tags which only differ in the isotope coding are chemically identical and are eluted virtually simultaneously in the HPLC; however, they differ in the mass spectrometer by the respective molecular weight differences due to the affinity labels having different isotope patterns. Relative protein concentrations can be obtained directly by carrying out measurements of the peak areas. Suitable affinity tags are conjugates composed of affinity tags (ligands), which are linked covalently to protein-reactive groups by way of bridge members. In connection with this, different isotopes are incorporated into the bridge members. An affinity ligand A is used for selectively enriching samples by means of affinity chromatography. The affinity columns are provided with the corresponding reactants which are complementary to the affinity ligands, and which enter into covalent or noncovalent bonds with the affinity ligands. An example of a suitable affinity ligand is biotin or a biotin derivative, which enters into strong, noncovalent bonds with the complementary peptides avidin or spectravidin. In this way, it is possible to use affinity chromatography to selectively isolate samples to be investigated from sample mixtures.

DEFINITIONS

The term "affinity tag" is used herein to refer to a chemical moiety that binds to a specific partner, which partner can be immobilized on a slide, bead, microtiter plate or the like. The affinity tag is preferably less than about 5000 Da. Examples include, but are not limited to, biotin, Brilliant Blue FCF (BB FCF), azorubine, phytoestrogen, digoxigenin, hormones, cytokines, dyes, and vitamins, which have a specific binding partner. Biotin, a small vitamin molecule (Mr 244), binds with high affinity (kD 10-15 M-1) to avidin, a protein largely distributed in egg whites (Mr 70,000), which can be conjugated to different markers such as fluorescent dyes, peroxidase, ferritin, and colloidal gold. Avidin, streptavidin and NeutrAvidin are available from Invitrogen, Inc. However, other tags are known for use in, e.g., chromatography, and may be adapted for use in accordance with the present teachings. These tags include IgG-protein A, phenyldiboronic acid-salicylhydroxamic acid, and metal tags for binding, e.g., to his-tags and GST (glutathione-S-transferase) tags. Six His-tags (MW ~900 Da) have an affinity for nickel or cobalt ions that are covalently bound to NTA (nitrilotriacetic acid) for the purposes of solid medium entrapment. A metal is attached to the affinity group (e.g., Ni, Co, Zn). Antibodies with high affinity/avidity may also be employed against hapten tags on the probe. KREATECH Biotechnology B.V. supplies high affinity monoclonal anti-Cyanine 3 and anti-Cyanine 5 antibodies, which may be immobilized and used to bind these dyes in the present linker system. Other dyes, such as Texas red, Rhodamine red, Oregon green 514 and fluorescein have been found to bind to certain peptides with high affinity. See, Rozinov et al., "Evolution of peptides that modulate the spectral qualities of bound, small-molecule fluorophores," *Chem Biol.* 1998 December; 5(12):713-28.

U.S. Pat. No. 6,884,815, "High affinity small molecule C5a receptor modulators," discloses small molecules, which could be used as affinity tags to immobilized C5a receptors.

In the same sense, it is also possible for example, to use carbohydrate residues, which are able to enter into noncovalent interactions with fixed lectins, for example, as affinity ligands. It is furthermore possible to use the interaction of haptens with antibodies, or the interaction of transition metals with corresponding ligands, as complexing agents, or other systems that interact with each other, in the same sense.

Alternatively, the selective enrichment can also be achieved by means of selective, reversible binding to an appropriately functionalized solid phase. Examples of suitable solid phases are amino-functionalized resins based on silica gel and, furthermore, those known from the peptide syntheses carried out as solid phase syntheses, such as trityl resin, Sasrin resin, which is based on benzyl alcohol supportation, Wang resin, which is based on benzyl alcohol supportation, Wang polystyrene resin, Rink amide MBHA resin or TCP (trityl chloride polystyrene) resin.

The term "diazo-aryl cleavable linker" is used herein to refer to a linker of the general formula aryl-N=N-aryl. As used herein, the term "aryl" refers to a monovalent "aromatic" (including heteroaromatic) carbocyclic radical. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl. The term aryl includes "substituted aryl" groups in which ring carbon atoms have additional substituents, such as methyl or other lower alkyl, amine, sulfur oxy, hydroxyl or nitrogen containing groups. Specifically included are substituted phenylazo groups where each linked phenyl group independently is substituted with hydroxy, alkyl, or carboxy. It is important that the linker have a hydroxyl group for cleavage to work and it needs to be in the ortho position relative to the diazo group. The linker may be represented as follows:

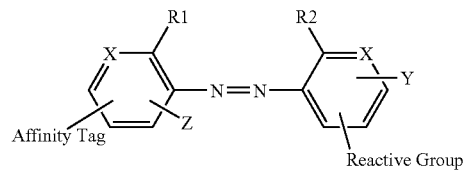

wherein at least one of R1 and R2 is OH. Y and Z indicate that the present activity of the cleavable linker is maintained with certain modifications to the aryl diazo structure. Tolerable substitutions include lower alkyl, hydroxyl, carboxy or keto. Although phenyl is the preferred aromatic group, i.e., X=C, other heteroaromatic groups may be used, e.g., pyridyl, X=N. X may also be S or O.

As used herein, the term "lower alkyl" refers to straight or branched chain alky compounds of C1-C10, optionally substituted with an oxy, hydroxyl, nitrogen, nitroxy, sulfhydryl or sulfide group.

The "reactive group," as defined below, may be linked through optional peptidyl or alkyl groups. The "affinity tag" is similarly as defined above, e.g., biotin, iminobiotin, etc., and may be linked to the above structure by peptidyl or alkyl linkers.

The term "reactive group" is used herein to refer to a probe which specifically binds to a compound, such as an enzyme, in a complex mixture of enzymes, with sufficient affinity and avidity to remove the enzyme from the mobile phase (e.g., cellular extract) to the immobilized phase (column, well, beads, etc.) onto which the probe is linked. In the preferred embodiment, the selection probe binds to a specific enzyme or class of enzymes, such as by covalent modification of the active site. Numerous examples of selection probes are given in Campbell and Szardenings, "Functional profiling of the proteome with affinity labels," Current Opinion in Chemical Biology 7:296-303 (2003), including probes to glycosyl hydrolases, serine hydrolases, cysteine proteases, tyrosine phosphatases, aldehyde dehydrogenase, thiolase, penicillin binding proteins, kinase (IKKβ), NF-κB, deubiquitinase, PAF-acetylase, and glucosidase.

The reactive group probes illustrated below are termed "SV1" and "SV31" and are based on an epoxysuccinyl group linked to a peptidyl group which is designed based the substrate of the enzyme to be bound by the probe. This class of protease inhibitors has been described in a number of publications, e.g., Czaplewski C. et al., "Binding modes of a new epoxysuccinyl-peptide inhibitor of cysteine proteases. Where and how do cysteine proteases express their selectivity?" *Biochim Biophys Acta.* 1999 May 18; 1431(2):290-305; Verhelst and Bogyo, "Solid-Phase Synthesis of Double-Headed Epoxysuccinyl Activity-Based Probes for Selective Targeting of Papain Family Cysteine Proteases," *ChemBioChem* 2005, 6, 1-4; Stern et al., "Crystal structure of NS-134 in complex with bovine cathepsin B: a two-headed epoxysuccinyl inhibitor extends along the entire active-site cleft," *Biochem. J.* (2004) 381 (511-517), etc.

Epoxide based selection probes are further described in the above-cited United States Patent Application 2006/0154325 to Bogyo, et al., and in Bogyo et al., US 2002/0150961 published Oct. 17, 2002, entitled "Activity-dependent cysteine protease profiling reagent," both of which are, as stated at the end of the specification, specifically incorporated by reference in their entirety.

Other reactive groups can be used besides epoxysuccinyl probes, e.g., Gelhaus et al., "Synthesis and antiplasmodial activity of a cysteine protease-inhibiting biotinylated aziridine-2,3-dicarboxylate," *Biol. Chem.* 385: 1431-6730 (2004).

Other reactive groups may be based on the acyloxymethyl ketone (AOMK) 'warhead' because of its reported high selectivity for cysteine proteases. Examples of these activity-based probes are found in Kato et al., "Activity-based probes that target diverse cysteine protease families," *Nature Chemical Biology* 1, 33-38 (2005).

The general epoxide scaffold for JPM-OEt is based on the natural product E-64, which was discovered to be a natural product inhibitor of cysteine protease in 1978 (Hanada, K. et al., *Agric. Biol. Chem.* 1978 42, 523-528 and 529-536).

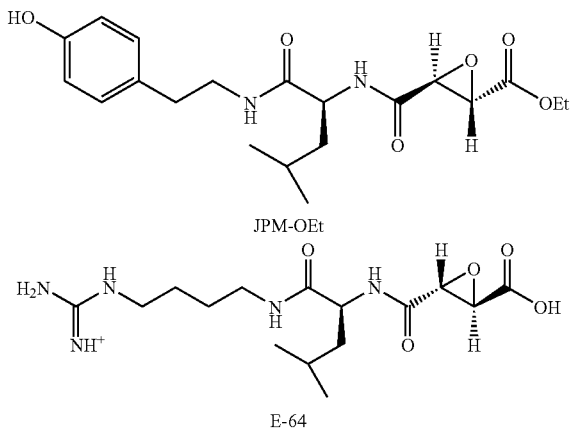

Still other reactive groups that are useful in the present invention are termed "protein reactive groups," as described in the above-cited US 2005/0049406 to Lerchen, Hans-Georg, et al., published Mar. 3, 2005, entitled "Isotopically coded affinity markers 3."

The Protein-reactive groups (PRG) are used for selectively labeling the proteins at selected functional groups in the ICAT technique. PRGs have a specific reactivity for terminal functional groups in proteins. Examples of amino acids that, as elements or proteins, are frequently used for selective labeling, are mercaptoaminomonocarboxylic acids, such as cysteine, diaminomonocarboxylic acids, such as lysine or arginine, or monoaminodicarboxylic acids, such as aspartic acid or glutamic acid. Furthermore, protein-reactive groups can also be phosphate-reactive groups, such as metal chelates, and also aldehyde-reactive and ketone-reactive groups, such as semicarbazones or else amines, accompanied by subsequent treatment with sodium borohydride or sodium cyanoborohydride. Protein-reactive groups can also be groups that, following a selective protein derivatization, such as a cyanogen bromide cleavage, or an elimination of phosphate groups, etc., react with the reaction products.

The present probes, containing reactive groups, are exemplified by peptide derivatives which are activity based probes (ABPs).

The term "peptide derivative" means a compound comprising an oligopeptide that may have modifications to peptide side chains and/or organic groups serving as linkers or spacers inserted between amino acids. The present peptides are preferably 1-5, preferably 1-3 amino acids, and will include various modifications and derivatives of naturally occurring amino acids, as well as non-natural amino acids. As is known, the naturally occurring amino acids are: Alanine, Arginine, Asparagine, Aspartic Acid, Cysteine, Glutamine, Glutamic Acid, Glycine, Histidine, Isoleucine, Leucine, Lysine, Methionine, Phenylalanine, Proline, Serine, Threonine, Tryptophan, Tyrosine, and Valine. They may include amino acid derivatives.

The term "amino acid derivative," such as may be a residue in a peptide derivative, includes, in addition to the modifications specifically illustrated below, derivatives such as -tyrosine methyl ester, L-3,5-diiodotyrosine methyl ester, L-3-iodotyrosine methyl ester, β-(4-hydroxy-naphth-1-yl)-L-alanine methyl ester, β-(6-hydroxy-naphth-2-yl)-L-alanine methyl ester, and the like, as are described in U.S. Pat. No. 6,949,570 to Ashwell et al., hereby incorporated by reference for purposes of describing the synthesis, structure and use of certain amino acid derivatives. Other examples of amino acid derivatives that may be utilized in the present methods and compounds are given in U.S. Pat. No. 6,900,196 to Liebeschuetz, et al., entitled "Serine protease inhibitors," U.S. Pat. No. 6,133,461 to Inaba, entitled "Process for producing amide derivatives and intermediates therefore," and U.S. Pat. No. 5,346,907 to Kerwin, Jr. et al., entitled "Amino acid analog CCK antagonists," all of which are hereby incorporated by reference in their entirety as describing exemplary amino acid analogs, modifications and derivative useable in the present methods.

The term "peptide" is used in its scientifically accepted sense to mean any compound produced by amide formation between a carboxyl group of one amino acid and an amino group of another. The amide bonds in peptides may be called peptide bonds. The word peptide usually applies to compounds whose amide bonds are formed between C-1 of one amino acid and N-2 of another (sometimes called eupeptide bonds), but it includes compounds with residues linked by other amide bonds (sometimes called isopeptide bonds).

The term "label" is used herein to refer to a small molecule or isotope that may be attached to the present ABPs. The label may be radioactive, chromogenic, fluorescent or the like. Fluorescent labels are preferred. The term "fluorophore" means a fluorescent molecule, i.e., one that emits electromagnetic radiation, especially of visible light, when stimulated by the absorption of incident radiation. The term includes fluorescein, one of the most popular fluorochromes ever designed, which has enjoyed extensive application in immunofluorescence labeling. This xanthene dye has an absorption maximum at 495 nanometers. A related fluorophore is Oregon Green, a fluorinated derivative of fluorescein. The term further includes bora-diaza-indecene, rhodamines, and cyanine dyes. The term further includes 5-EDANS Nucleotide Analogs, Adenosine 5'-triphosphate [g]-1-Naphthalenesulfonic acid-5(2-Aminoethylamide) (ATP[g]-1,5-EDANS) and 8-Azidoadenosine 5'-triphosphate [g]-1-Naphthalenesulfonic acid-5(2-Aminoethylamide) (8N3ATP [g]-1,5-EDANS).

The term "bora-diaza-indecene" means compounds represented by 4,4-difluoro-4-bora-3a,4a-diaza-s-indacene, known as BODIPY® dyes. Various derivatives of these dyes are known and included in the present definition, e.g., Chen et al., "4,4-Difluoro-4-bora-3a,4a-diaza-s-indacene (BODIPY) dyes modified for extended conjugation and restricted bond rotations," *J Org Chem.* 2000 May 19; 65(10):2900-6. These compounds are further defined in reference to the structures set out below under the heading "FLUOROPHORES."

The term "rhodamine" means a class of dyes based on the rhodamine ring structure. Rhodamines include (among others): Tetramethylrhodamine (TMR): a very common fluorophore for preparing protein conjugates, especially antibody and avidin conjugates; and carboxy tetramethyl-rhodamine (TAMRA), used for oligonucleotide labeling and automated nucleic acid sequencing. Rhodamines are established as natural supplements to fluorescein based fluorophores, which offer longer wavelength emission maxima and thus open opportunities for multicolor labeling or staining. The term is further meant to include "sulfonated rhodamine," series of fluorophores known as Alexa Fluor dyes.

The dramatic advances in modern fluorophore technology are exemplified by the Alexa Fluor dyes introduced by Molecular Probes (Alexa Fluor is a registered trademark of Molecular Probes). These sulfonated rhodamine derivatives exhibit higher quantum yields for more intense fluorescence emission than spectrally similar probes, and have several additional improved features, including enhanced photostability, absorption spectra matched to common laser lines, pH insensitivity, and a high degree of water solubility.

The term "cyanine" means a family of cyanine dyes, Cy2, Cy3, Cy5, Cy7, and their derivatives, based on the partially saturated indole nitrogen heterocyclic nucleus with two aromatic units being connected via a polyalkene bridge of varying carbon number. These probes exhibit fluorescence excitation and emission profiles that are similar to many of the traditional dyes, such as fluorescein and tetramethyl-rhodamine, but with enhanced water solubility, photostability, and higher quantum yields. Most of the cyanine dyes are more environmentally stable than their traditional counterparts, rendering their fluorescence emission intensity less sensitive to pH and organic mounting media. In a manner similar to the Alexa Fluors, the excitation wavelengths of the Cy series of synthetic dyes are tuned specifically for use with common laser and arc-discharge sources, and the fluorescence emission can be detected with traditional filter combinations.

Marketed by a number of distributors, the cyanine dyes are readily available as reactive dyes or fluorophores coupled to a wide variety of secondary antibodies, dextrin, streptavidin, and egg-white avidin.

The term "mild reducing agent" is used here in its scientifically accepted sense, and includes the exemplified sodium dithionite, thiosulfate, DTT, 2-mercaptoethanol, sodium borohydride in methanol, etc. The present linkages are sensitive towards dithionite agents and the like, which are compatible with aqueous, buffered solutions. Powerful reductants will not work as well due to their sensitivity for water and other proton sources.

EXAMPLES

General Methods

Unless otherwise noted, all reagents were purchased from commercial suppliers and used without further purification. All solvents used were of HPLC grade. Reactions were analyzed by thin-layer chromatography on Whatman 0.25 mm silica plates with fluorescent indicator or LC-MS. Flash chromatography was carried out with EMD 230-400 mesh silica gel. Reverse-phase HPLC was conducted on a C18 column using the AKTA explorer 100 (Amersham Pharmacia Biotech). Purifications were performed at room temperature and compounds were eluted with increasing concentration of acetonitrile (solvent A: 0.1% TFA and 5% acetonitrile in water, solvent B: 0.1% TFA in water). High-resolution MS analyses were performed by Stanford Proteomics and Integrative Research Facility using a Bruker Autoflex MALDI TOF/TOF mass spectrometer. LC/MS data were acquired using an API 150EX LC/MS system (Applied Biosystems) using a general gradient of 5-100% acetonitrile. Protein identification was performed on a LCQ DecaXP+ mass spectrometer (Thermo Electron) coupled to an Agilent 1100 LC unit. Chromatographic separation of the digested peptides was performed on a Picofrit BioBasic C18 column (10 cm×75 µm i.d.) (New Objective) (solvent A: 0.1% formic acid in water, solvent B: 0.1% formic acid in acetonitrile) Gradient from 2-50% of solution B was used for elution.

Solid Phase Synthesis.

Figure 2:
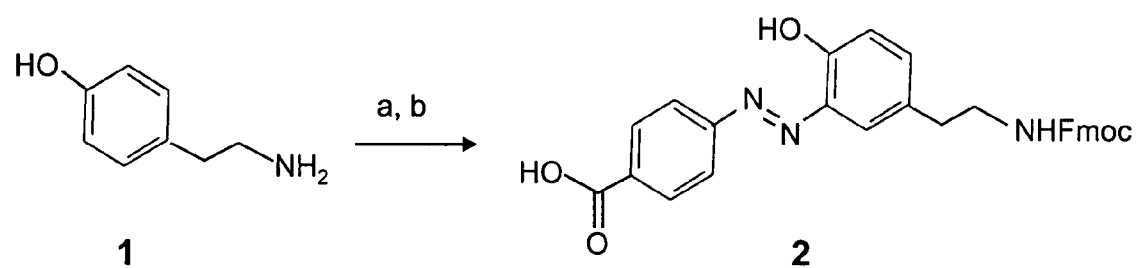
FIG. 2 is a reaction scheme showing synthesis of the diazobenzene cleavable linker building block Fmoc-CL-OH.

Diazobenzene derivatives are readily accessible from diazonium salts and phenols. Referring now to FIG. 2, compound 1 m-aminoethyl phenol is reacted to produce the cleavable linker building block Fmoc-CL-OH (compound 2). The reaction utilizes the following reagents and conditions: a) 4-carboxy benzene diazonium chloride (2 eq.), aq. NaHCO3, o/n, then b) Fmoc-chloride (1.1 eq.), 59% (2 steps).

In brief, compound 2 can be made by a diazonium coupling of tyramine (1) and 4-carboxy-benzenediazonium chloride. Next, a Fmoc-group is installed on the free amino function, yielding the desired product in 59% after silica column purification.

Figure 3:
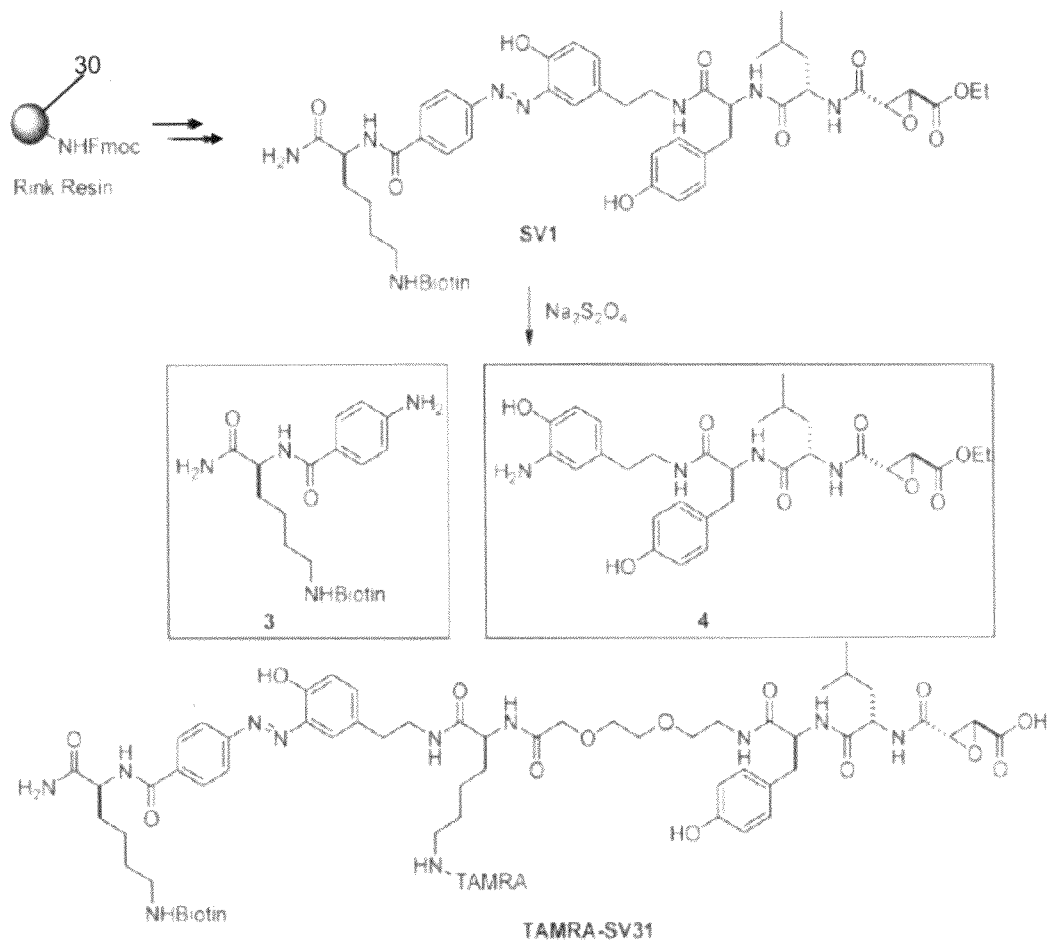
FIG. 3 is a reaction scheme showing synthesis of probes and their chemoselective cleavage.

Using solid phase peptide synthesis protocols, the diazobenzene cleavable linker was incorporated into the activity based probe SV1 (FIG. 3), analogous to the previously reported general papain-family probe DCG-04.[9] FIG. 3 shows that compound 2 was immobilized on a Rink resin indicated at 30. Then, the Fmoc protective group was removed and the ABP designated SV1, having the known epoxysuccinyl "warhead" attached to a peptide derivative. Such compounds are disclosed, for example in United States Patent Application 2006/0154325 to Bogyo, et al., published Jul. 13, 2006, entitled "Synthesis of epoxide based inhibitors of cysteine proteases."

Probes were synthesized with a slight modification from previously published procedures. (Greenbaum, D.; Medzihradszky, K. F.; Burlingame, A.; Bogyo, M. *Chem. Biol.* 2000, 7, 569-581; 1. Verhelst, S. H. L.; Bogyo, M. *Chembiochem* 2005, 6, 824-827). Solid phase peptide synthesis was performed on Rink resin, using Fmoc-amino acid/DIC/HOBt (3 eq/3 eq/3 eq with respect to the loading reported by the supplier) in DMF (approximately 0.3 M) for 1-2 h at room temperature. Fmoc-CL-OH (1.5 eq.; overnight) and all subsequent building blocks were coupled with PyBOP/DIEA, a stronger coupling agent ensuring quick and quantitative coupling also in the presence of the unprotected phenol function on the cleavable linker. Fmoc protecting groups were removed with piperidine/DMF 1/4 (15 min). The epoxysuccinate warhead was introduced by reaction with 1.3 eq. of ethyl p-nitrophenyl (2S,3S)-oxirane-2,3-dicarboxylate (Chehade, K. A. H.; Baruch, A.; Verhelst, S. H. L.; Bogyo, M. Synthesis 2005, 240-244). The probes were cleaved by incubation with a solution of TFA:TIS:H$_2$O (95%:2.5%:2.5%) for 1 hour. Cleavage solution was evaporated to dryness and purified by HPLC.

Example 1

Preparation of 4-[5-(N-fluorenyloxycarbonyl-2-Amino-ethyl)-2-hydroxy-phenylazo]-benzoic acid (Compounds 1 and 2 in FIG. 2)

A solution of 4-carboxy-benzenediazonium chloride was prepared in the following way. Solid NaNO$_2$ (345 mg, 5 mmol, 5 eq.) was added to a cooled suspension of 4-aminobenzoic acid (274 mg, 2 mmol, 2 eq.) in 6 M HCl (4 mL). The resulting mixture was stirred at 0° C. and turned into a slightly yellow-brownish solution. After 15 min the diazonium salt solution was slowly added to a solution of tyramine (137 mg, 1 mmol) in aqueous saturated bicarbonate. The pH of the reaction was kept basic by repeated addition of sodium bicarbonate. The mixture was allowed to slowly warm up to room temperature and was stirred overnight. Next, Fmoc-chloride (285 mg, 1.1 mmol, 1.1. eq) was added. After 1 h, the reaction was acidified with concentrated HCl. The formed solids were filtered and the filtrate was extracted with EtOAc, washed with water, dried over MgSO$_4$ and concentrated under reduced pressure. Solids from extraction and filtration were combined and dry-loaded on a silica column, which was eluted with 0-10% MeOH in dichloromethane/acetic acid 99/1, yielding the title product as an orange-red solid (300 mg, 59% yield). The purity was sufficient for routine solid phase chemistry. An aliquot was further purified for analytical analysis. ESI-MS: 508.3 [M+H]$^+$ $^1$H NMR (500 MHz, dmso-d$_6$): δ 10.88 (s, 1H), 8.10 (d, 2H, J=8.6 Hz), 8.03 (d, 2H, J=8.6 Hz), 7.87 (d, 2H, J=7.6 Hz), 7.64 (d, 2H, J=7.2 Hz), 7.59 (d, 1H, J=1.8 Hz), 7.42-7.37 (m, 3H), 7.31-7.27 (m, 3H), 7.01 (d, 1H, J=8.4 Hz), 4.27 (d, 2H, J=7.1 Hz), 4.19 (t, 1H, J=7.0 Hz), 3.26-3.21 (m, 2H), 2.72 (t, 2H, J=6.8 Hz). HRMS: found [M+H]$^+$ 508.1700. C$_{30}$H$_{26}$N$_3$NaO$_5^+$ requires 508.1872.
SV1

Orange-yellow solid. 30% yield after HPLC purification. ESI-MS: 1057.6 [M+H]$^+$ $^1$H NMR (500 MHz, dmso-d$_6$): δ 10.92 (bs, 1H), 9.18 (bs, 1H), 8.55-8.50 (m, 2H), 8.12 (d, 1H, J=8.3 Hz), 8.09 (d, 2H, J=8.7 Hz), 8.04 (d, 2H, J=8.4 Hz), 8.00 (t, 1H, J=5.3 Hz), 7.79 (t, 1H, J=5.3 Hz), 7.61 (s, 1H), 7.47 (s, 1H), 7.27 (d, 1H, J=8.4 Hz), 7.06 (s, 1H), 7.00 (d, 1H, J=8.2 Hz), 6.94 (d, 2H, J=8.3 Hz), 6.59 (d, 2H, J=8.3 Hz), 6.45 (bs, 1H), 6.38 (bs, 1H), 4.40-4.26 (m, 4H), 4.20-4.15 (m, 2H), 4.12-4.08 (m, 1H), 3.71 (d, 1H, J=1.3 Hz), 3.59 (d, 1H, J=1.3 Hz), 3.38-3.32 (m, 1H), 3.23-3.18 (m, 1H), 3.09-3.02 (m, 3H), 2.82-2.74 (m, 2H), 2.66-2.61 (m, 3H), 2.58-2.54 (m, 1H), 2.02 (t, 2H, J=7.1 Hz), 1.81-1.70 (m, 2H), 1.62-1.54 (m, 1H), 1.52-1.25 (m, 12H), 1.22 (t, 3H, J=7.1 Hz), 0.85 (d, 3H, J=6.6 Hz), 0.82 (d, 3H, J=6.6 Hz). HRMS: found [M+H]$^+$ 1057.4912. C$_{52}$H$_{69}$N$_{10}$O$_{12}$S$^+$ requires 1057.4817.
SV31

Orange-yellow solid. 17% yield after HPLC purification. ESI-MS: 1303.1 [M+H]$^+$ $^1$H NMR (500 MHz, dmso-d$_6$): δ 10.94 (bs, 1H), 9.17 (bs, 1H), 8.54-8.49 (m, 2H), 8.21 (t, 1H, J=5.3 Hz), 8.11 (d, 2H, J=8.5 Hz), 8.06 (d, 2H, J=8.5 Hz), 7.96 (t, 1H, J=5.5 Hz), 7.79 (t, 1H, J=5.5 Hz), 7.66-7.58 (m, 3H), 7.48 (s, 1H), 7.30 (dd, 1H, J=8.3 Hz, J=2.1 Hz), 7.06 (s, 1H), 7.01 (d, 1H, J=8.5 Hz), 6.97 (d, 2H, J=8.4 Hz), 6.61 (d, 2H, J=8.4 Hz), 6.45 (bs, 1H), 6.38 (bs, 1H), 4.42-4.26 (m, 5H), 4.12-4.08 (m, 1H), 3.91 (s, 2H), 3.66 (d, 1H, J=1.8 Hz), 3.60-3.55 (m, 2H), 3.54-3.50 (m, 2H), 3.47 (d, 1H, J=1.7 Hz), 3.40-3.22 (m, 5H), 3.17-3.12 (m, 1H), 3.08-2.99 (m, 3H), 2.85-2.76 (m, 2H), 2.73-2.66 (m, 5H), 2.57-2.52 (m, 1H), 2.02 (t, 2H, J=7.4 Hz), 1.78-1.71 (m, 2H), 1.64-1.55 (m, 2H), 1.53-1.18 (m, 17H), 0.85 (d, 3H, J=6.6 Hz), 0.81 (d, 3H, J=6.5 Hz). HRMS: found [M+H]$^+$ 1302.6688. C$_{62}$H$_{88}$N$_{13}$O$_{16}$S$^+$ requires 1302.6193.

Example 2

Capture and Release of Proteases from Cell Lysate

We initially tested the cleavage of SV1 (shown in FIG. 3) by incubation with 100 mM Na$_2$S$_2$O$_4$. After 30 minutes full cleavage of SV1 into the two aniline fragments 3 and 4 (FIG. 3) was observed using LC-MS analysis.

We next investigated the capture and release of proteases that could be selectively labeled in a complex proteome. For this analysis, the related probe SV31 (FIG. 3, bottom) was constructed to contain an additional PEG-linker (CH$_2$—O—C$_2$H$_4$—O—C$_2$H$_4$—) and a free epoxysuccinate (instead of OEt) for increased hydrophilicity. In addition, a fluorophore (TAMRA) was introduced on the side of the probe that remains attached to the target enzymes. This feature allows rapid in gel fluorescent detection after on-bead cleavage of the diazobenzene linker and subsequent resolution by SDS-PAGE.

Figure 4:
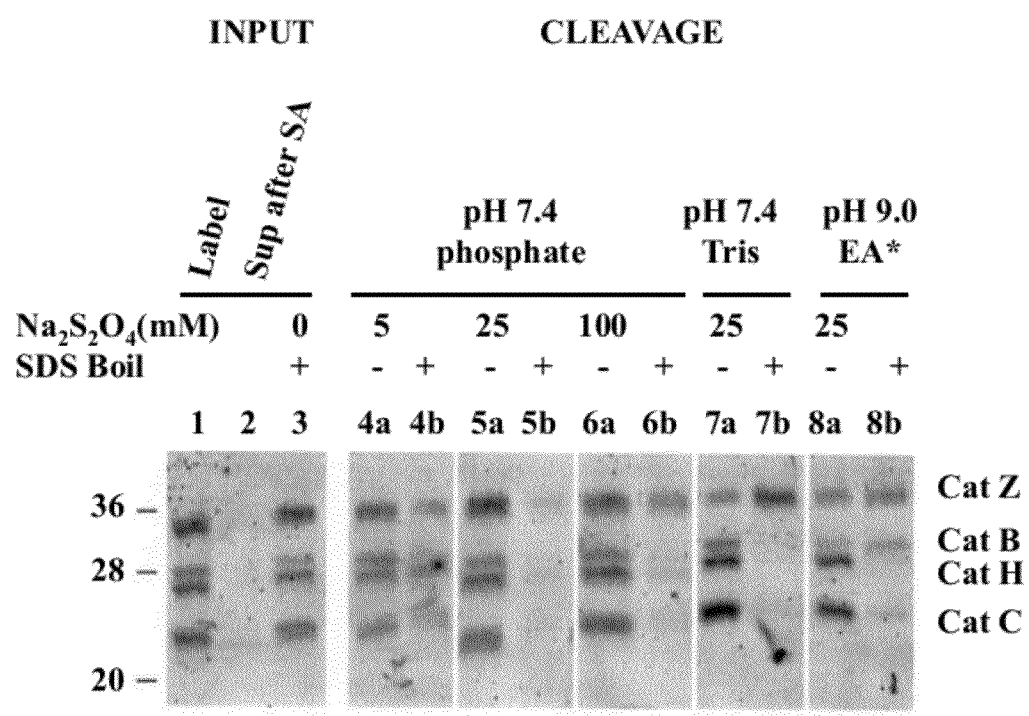
FIG. 4 is a series of gels showing optimization of the chemoselective cleavage from streptavidin. The four major cathepsin activities in rat liver homogenate were labeled by the general papain probe (lane 1) and are depleted from the mixture by incubation with streptavidin-beads (lane 2). Lane 3 shows that non-selective denaturing conditions release all proteins from the SA. Different conditions for selective cleavage (lanes 4-8) are more or less effective in releasing the labeled peptides, with condition 5 cleaving over 90%. EA: ethanolamine.

Accordingly, rat liver homogenate, which contains a number of previously characterized cathepsin activities,[10] was incubated with tetramethylrhodamine (TAMRA) tagged SV31 for 1 h and excess probe was removed by filtration over a size exclusion column. The resulting eluate showed clean labeling of the four major cathepsins present in the proteome. This is shown in FIG. 4. FIG. 4 shows gel fluorescent detection of four species of cathepsin, as shown in Table 1 below. Lane 1 shows labeling of the liver homogenate with the probe. Incubation with immobilized streptavidin efficiently depleted labeled enzymes from the supernatant (lane 2). Non-selective cleavage by denaturation of streptavidin with boiling in SDS buffer resulted in near quantitative release of the labeled proteases (lane 3).

Although SnCl$_2$ was able to cleave the diazobenzene linker (data not shown), this reagent required 0.1 M hydrochloric acid as a solvent. Therefore, we turned our attention to sodium dithionite, which can be used in milder buffers. After treatment with the chemoselective cleavage cocktail (3×15 minutes 7c; lanes a), the proteases remaining on the beads were cleaved off by boiling with SDS sample buffer (lanes b, in the concentrations of dithionite indicated in the top row of FIG. 4). Interestingly, the use of no buffer or low pH buffers reduced cleavage efficiency significantly (data not shown). After testing a range of dithionite concentrations (lane 4-6), the optimal conditions were found to be 25 mM Na2S2O4 at pH 7.4 (lane 5a). Densometry of the lanes by image analysis software revealed that approximately 91% of the protein is recovered upon specific cleavage (determined by the ratio of the a and b lanes and averaged over three independent runs). Surprisingly, at higher pH, or when Tris was used as a buffer, the cleavage of the higher molecular weight cathepsins was less efficient (lanes 7 and 8).

Rat liver lysate (300 µg total protein) in reaction buffer (50 mM acetate pH 5.5, 2 mM DTT, 5 mM MgCl$_2$) was incubated for 1 h with tetramethylrhodamine (TAMRA) tagged SV30 (2 µM final concentration, from a 100×DMSO stock solution). Labeled protein was separated from unreacted probe by filtration over a protein desalting spin column (Pierce, Rockford, Ill., USA), which was equilibrated with phosphate buffer (100 mM, pH 7.4). Eluate was added to 100 µL immobilized streptavidin slurry (UltraLink® Immobilized Streptavidin, Pierce) and gently vortexed for 1 h. Streptavidin beads were washed with phosphate buffer (3×), divided into six 20 µL aliquots and gently vortexed in the presence of 20 µL cleavage cocktail (25 mM $Na_2S_2O_4$ in buffers of different pH) for 15 minutes. Supernatant was collected and cleavage was repeated two times. Pooled cleavage supernatants were treated with 4×SDS sample buffer. Next, streptavidin beads were washed with phosphate buffer (3×) and boiled with SDS sample buffer. One fourth of the sample (corresponding to 15 µg of total protein) was loaded on a 15% SDS-PAGE gel and labeled proteins were visualized using a typhoon 9410 scanner (Amersham Bioscience) with excitation at 532 nm and detection at 580 nm.

Mass Spectrometric Analysis of Released Proteins

Rat liver homogenate (20 mg of total protein) in reaction buffer was incubated with SV1 (10 µM) for 2 h. Unreacted probe was removed by filtration over a PD10 column (Amersham Bioscience) and the eluate (in PBS buffer) was shaken with immobilized streptavidin slurry (20 µL) for 1 h. The streptavidin beads were subsequently washed with PBS buffer containing 1M NaCl, 0.1% SDS and 10% EtOH (3× each). Proteases labeled by the probe were cleaved off with $Na_2S_2O_4$ using the above-described procedure. The pooled supernatant was denatured by incubating with 1 volume of 12 M urea. Next, disulfide bonds were reduced with DTT (10 mM, 60 minutes) and free cysteines were capped with iodoacetamide (40 mM, 60 minutes). Unreacted iodoacetamide was neutralized by addition of an equal amount of DTT and the concentration of urea was lowered to 2 M by addition of water. Trypsin digestion was performed overnight at 37° C. (0.1 µg of trypsin). Digestion was stopped by addition of formic acid (5% final concentration) and digested samples were desalted using a C18 Zip-Tip (Millipore) prior to LC/MS-MS analysis. Data was analyzed by the Sequest algorithm (Novatia) and evaluated by Scaffold (Proteome Software Inc.). Peptides with probability value>95% (in Scaffold) were considered positive hits.

Although the optimized release of probe-labeled proteins from streptavidin using dithionite is slightly lower in efficiency than under denaturing conditions, this method is likely to result in less background signals leading to easier identification of the target proteases. In addition the direct on-bead cleavage method using a mass spectrometry-compatible buffer allows direct in solution digestion of samples followed by MS analysis. To confirm these issues we analyzed the samples in FIG. 2 by direct solution digestion with trypsin followed by LC-MS/MS analysis of all peptide products. This analysis identified multiple peptides from each of the expected cathepsin proteases without any contamination by background proteins (Table 1). These results suggest that the mild cleavage conditions are compatible with mass spectrometry methods. Furthermore, the highly selective cleavage reduces background signal and provides a straight forward means to avoid gel-based separation methods. A more comprehensive and detailed analysis is reported in Fonović et al., Proteomic evaluation of chemically cleavable activity based probes," Mol. and Cell Proteomics Manuscript M700-124-MCP200 (published online Jul. 5, 2007).

TABLE 1

Identified proteases targeted by SV1 after chemoselective release from immobilized streptavidin

| Protein | Molecular mass | Number of Identified peptides | Sequence coverage |
| --- | --- | --- | --- |
| Cathepsin Z | 34 kDa | 4 | 32% |
| Cathepsin B | 29 kDa | 2 | 8% |
| Cathepsin H | 24 kDa | 5 | 29% |
| Cathepsin C | 26 kDa | 3 | 16% |

Example 3

Figure 5:
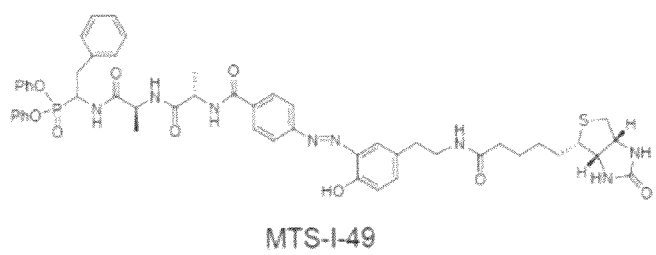
FIG. 5 is a structural formula of a peptidyl aminoalkylkanephosphonate inhibitor with a cleavable linkage (a), and a photograph of gels run with the compound of (a), where mouse liver extracts were labeled with MTS-I-49 containing the present cleavable linker and analyzed by direct SDS-PAGE followed by biotin blotting.
Figure 5:
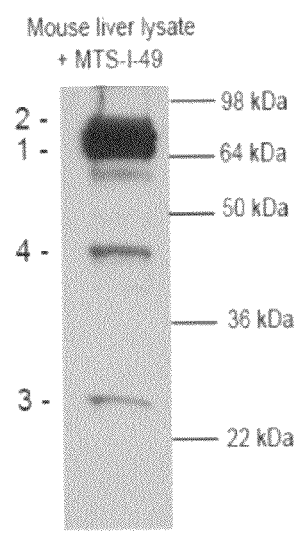

Cleavable Linker System Containing Phosphonate Reactive Group: MTS-I-49 Peptidyl Aminoalkanephosphonate To show applicability of the cleavable linker approach for profiling of other catalytic classes of proteases in the context of other probe scaffolds, we incorporated the diazobenzene linker into the peptide backbone of the commercially available probe DAP22C to make the probe MTS-I-49 (Enzyme Systems Products, USA; This structure is shown in FIG. 5a. The reactive group is shown in oval 52 and the affinity tag, which is biotin, is shown in rectangle 50. DAP22C (the active agent) is a peptidyl aminoalkanephosphonate that has been reported to target the serine proteases cathepsin G and chymotrypsin in vitro (Oleksyszyn, J., and Powers, J. C. (1991) Irreversible inhibition of serine proteases by peptide derivatives of (alpha-aminoalkyl)phosphonate diphenyl esters. Biochemistry 30, 485-493). However, it has not been used for any proteomic applications. We used MTS-I-49 to label mouse liver extracts and analyze the labeled sample by both SDS-PAGE (FIG. 5B) and by direct chemical cleavage or on bead digestion.

After enrichment on immobilized avidin, each of the three labeled proteomes (FIG. 5b) was divided into two aliquots. One was prepared for LC-MS/MS analysis by "on bead" digestion, while the other was chemically eluted and digested "in solution." Proteins identified in each tissue lysate are listed with their accession number and theoretical molecular weight (MW). To compare both approaches, the number of identified peptides and percentage of amino acid sequence coverage is listed for each protein.

The results of the on-bead digestion and chemical cleavage are shown in the Table below:

TABLE 2

| Protein | Accession Number | MW | Chemical Cleavage | On Bead Digestion |
| --- | --- | --- | --- | --- |
| Liver carboxylesterase 4 | gi|15488664 | 62 kDa | 14 (38%) | 20 (51%) |
| propionyl-Coenzyme A carboxylase | gi|13905236 | 80 kDa | 3 (8%) | 22 (45%) |
| glutathione-S-transferase | gi|2832492 | 25 kDa | 2 (12%) | 8 (44%) |
| acetyl-Coenzyme acyltransferase 2 | gi|20810027 | 42 kDa | 2 (15%) | 5 (26%) |
| carbonmonoxy hemoglobin | gi|18655689 | 16 kDa | 0 | 7 (68%) |
| betaine-homocysteine methyltransferase | gi|22477957 | 45 kDa | 0 | 4 (19%) |
| hemoglobin alpha 1 | gi|12846939 | 15 kDa | 0 | 3 (25%) |
| acetyl-Coenzyme A dehydrogenase | gi|26348293 | 19 kDa | 0 | 3 (34%) |
| albumin 1 | gi|26340966 | 69 kDa | 0 | 2 (6%) |

TABLE 2-continued

| Protein | Accession Number | MW | Chemical Cleavage | On Bead Digestion |
|---|---|---|---|---|
| alcohol dehydrogenase 1 | gi\|32449839 | 40 kDa | 0 | 3 (20%) |
| glyceraldehyde-3-phosphate dehydrogenase | gi\|55153885 | 36 kDa | 0 | 2 (10%) |
| 3-hydrozy-3-methylglutaryl-coenzyme A-synthase | gi\|12836439 | 57 kDa | 0 | 2 (6%) |
| carbamoyl-phosphate synthase 1 | gi\|82879179 | 165 kDa | 0 | 2 (2%) |
| fructose-bisphosphate aldolase | gi\|15723268 | 40 kDa | 0 | 2 (6%) |
| methionine adenosyltransferase 1 | gi\|74150290 | 44 kDa | 0 | 2 (9%) |
| peroxisomal acyl-CoA oxidase | gi\|2253380 | 75 kDa | 0 | 2 (4%) |
| glycine N-methyltransferase | gi\|15679953 | 33 kDa | 0 | 2 (10%) |

Proteins in the above Table were identified by LC/MS/MS analysis of on bead digested or chemically eluted proteins from mouse liver extracts labeled with MTS-I-49. A hypothetical protein was identified as the primary probe target after chemical cleavage. BLAST database searching identified it as liver carboxylesterase 4. A number of additional endogenously biotinylated proteins were identified in the on-bead digested sample.

The four most intensely labeled proteins from the gel image in FIG. 5B likely represent the top four hits in the m/s analysis based on predicted molecular weights.

Carboxylesterase 4 has not been characterized on a functional level and has never been confirmed to be catalytically active (Rawlings, N. D., Morton, F. R., and Barrett, A. J. (2006) MEROPS: the peptidase database. Nucleic Acids Res 34, D270-272.). It is not clear why we were only able to identify this one esterase but the lack of other reasonable targets in the on-bead digestion sample suggest that the probe may simply be inefficient or highly selective for targets that are not active in mouse liver extracts. While the on-bead digest identified a large number of background and endogenously biotinylated proteins, the chemical cleavage revealed predominant recovery of the S9 family clan SC serine hydrolyase, carboxylesterase 4. Overall the level of background peptides was decreased by over 90%, when chemical elution was used for the sample preparation (as shown in the above Table). Although the number of carboxylesterase peptides identified was reduced compared to the on-bead sample we could still make a confident identification with nearly 40% coverage of peptide sequence.

The above results show the applicability of the present chemically cleavable linker system to a peptidyl phenyl phosphonate. A number of phenyl phosphonate reactive groups (for activity based probes) are known and adaptable to the present materials and methods in view of the present teachings. See, for example U.S. Pat. No. 5,543,396 to Powers, et al., issued Aug. 6, 1996, entitled "Proline phosphonate derivatives;" Sieńczyk et al., "Inhibition of trypsin and urokinase by Cbz-amino(4-guanidinophenyl)methanephosphonate aromatic ester derivatives: The influence of the ester group on their biological activity," Bioorganic & Medicinal Chemistry Letters Volume 16, Issue 11, 1 Jun. 2006, Pages 2886-2890; Marnett et al., "Communication between the active sites and dimer interface of a herpesvirus protease revealed by a transition-state inhibitor," Proc. Nat. Acad. Sci. 101(18): 6870-6875 (May 2004), etc.

Synthesis (2'-Chloro)-chlorotrityl resin was treated with Fmoc-protected alanine under standard solid phase synthesis conditions (4 eq. DIEA in methylene chloride). The chain was extended under standard conditions using Fmoc-protected alanine (3 eq. HBTU, 3 eq. HOBT, 6 eq. DIEA), 4-(5-(2-N-Fmoc ethyl)-2-hydroxyphenylazo) benzoic acid (1.5 eq. PYBOP, 3.0 eq DIEA) and biotin (1.5 eq. PYBOP, 3.0 eq DIEA) sequentially, gently shaking in DMF. Removal of Fmoc protecting groups was performed with 20% piperidine in DMF at room temperature. Cleavage from the resin with 2% TFA in methylene chloride (10×2 ml) provided the free acid which was concentrated in vacuo and used directly without further purification. The above acid was treated with (1-amino-2-phenylethyl)phosphonic acid diphenyl ester (1 eq.), PYBOP (1.5 eq.) and DIEA (3 eq.) in DMF. The solution was stirred at room temperature overnight to provide MTS-I-49, which was purified by HPLC.

Example 4

Preparation of Cleavable Linker with Succinimide Reactive Group

Figure 6:
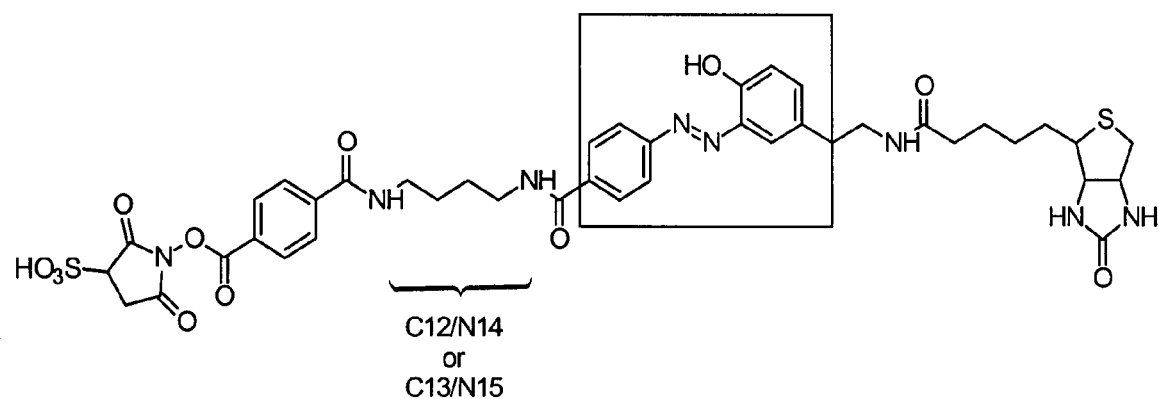
FIG. 6 is a structure showing an embodiment of the cleavable linker system in which in alkyl spacer has been inserted between the aryl-N=N-aryl structure and the Reactive Group, which in this case sulfo-N-hydroxy succinimide (S—NHS), as indicated by the bracket, providing atoms which can be isotopes such as C12/N14 and/or C13/N15.

This example describes the preparation of a compound such as illustrated in FIG. 6. As described in detail below, the compound (14) synthesized in this example does not have a spacer between the aryl group and the reactive group, whereas, the compound shown in FIG. 6 has a lower alkyl spacer which is indicated by the bracket and the notation "C12/N14 or C13/N15." this indication reflects the possibility of substituting isotopes of carbon and or nitrogen in the atoms indicated by the bracket. These isotopes may be incorporated into different cleavable linkers, on the reactive group side of the linker. This enables, for example, the quantitation of proteins by mass spectrometry. Stable (e.g. non-radioactive) heavier isotopes of carbon (C13) or nitrogen (N15) are incorporated by means of the reactive group into one sample while the other one is labelled with corresponding light isotopes (e.g. C12 and N14). The two samples are mixed before the analysis. Peptides derived from the different reactive group-linkers can be distinguished due to their mass difference. The ratio of their peak intensities corresponds to the relative abundance ratio of the peptides (and proteins). This is akin to popular methods for isotope labelling such as SILAC (stable isotope labelling with amino acids in cell culture), trypsin-catalyzed O18 labeling, ICAT (isotope coded affinity tagging), ITRAQ (isotope tags for relative and absolute quantitation). The use of the present compounds in ICAT analysis is discussed above.

4-[5-(N-fluorenyloxycarbonyl-2-Aminoethyl)-2-hydroxyphenylazo]-benzoic acid (10)

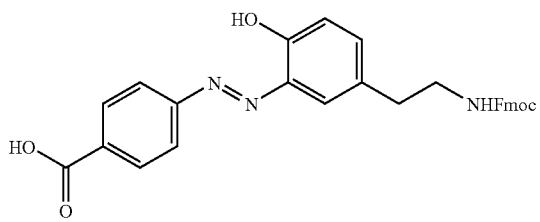

The formula below (compound 10) represents the same compound as compound 2 in FIG. 2. This compound has utility as an intermediate in the synthesis of a variety of cleavable linkers of the present invention. The alkyl group joining the protected amine can be varied, as well as the protective group used, as is known in the art. Thus, Fmoc may be replaced by other protective groups, such as Boc and Cbz. Of course, any other amino protecting group used in peptide synthesis, e.g., acyl residues of carbonic acid half-esters, especially tert.butyloxycarbonyl, benzyloxycarbonyl (optionally substituted), 2-halogenloweralkoxycarbonyl or allyloxycarbonyl are to be considered as within the term "PG". The present intermediates may be represented by the formula

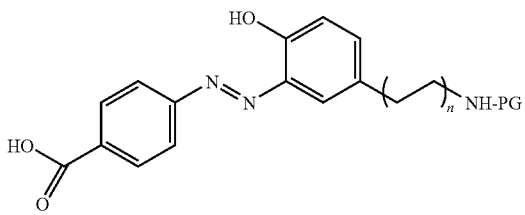

where n represents the number of atoms in the lower alky linking group and may be between 0 and 5, and "PG" represents an amine protective group, e.g. Fmoc, Boc, Cbz, etc. Further description of protective groups may be found in U.S. Pat. No. 5,549,974 to Holmes, issued Aug. 27, 1996, entitled "Methods for the solid phase synthesis of thiazolidinones, metathiazanones, and derivatives thereof."

A solution of 4-carboxy-benzenediazonium chloride was prepared in the following way. Solid $NaNO_2$ (345 mg, 5 mmol, 5 eq.) was added to a cooled suspension of 4-aminobenzoic acid (274 mg, 2 mmol, 2 eq.) in 6 M HCl (4 mL). The resulting mixture was stirred at 0° C. and turned into a slightly yellow-brownish solution. After 15 min the diazonium salt solution was slowly added to a solution of tyramine (137 mg, 1 mmol) in aqueous saturated bicarbonate. The pH of the reaction was kept basic by repeated addition of solid sodium bicarbonate. [N.B. note that the reaction mixture will foam a lot. It is best to take a relatively large reaction flask for this reaction]. The mixture was allowed to slowly warm up to room temperature and was stirred overnight. [N.B. at this point, the reaction will have turned into a dark red solution. You can follow the progression of the reaction by LCMS, which should give a peak of m/z=286.1 $[M+H]^+$ and 269.1 (fragment peak)]. Next, Fmoc-chloride (285 mg, 1.1 mmol, 1.1. eq) was added. After 1 h, the reaction was acidified with concentrated HCl. The formed solids were filtered and the filtrate was extracted with EtOAc, washed with water, dried over $MgSO_4$ and concentrated under reduced pressure. [N.B. the purification is somewhat tedious, as the compound does not dissolve very well in many solvents. It is preferred to pre-absorb in on a little bit of silica and dry-load onto a column for chromatography].

Solids from extraction and filtration were combined and dry-loaded on a silica column, which was eluted with 0-10% MeOH in dichloromethane/acetic acid 99/1, yielding the title product as an orange-red solid (300 mg, 59% yield). [N.B. This was one of the better purification methods, and gave improved yields.]

The purity was sufficient for routine solid phase chemistry. An aliquot was further purified for analytical analysis. ESI-MS: 508.3 $[M+H]^+$ $^1$H NMR (500 MHz, dmso-$d_6$): δ 10.88 (s, 1H), 8.10 (d, 2H, J=8.6 Hz), 8.03 (d, 2H, J=8.6 Hz), 7.87 (d, 2H, J=7.6 Hz), 7.64 (d, 2H, J=7.2 Hz), 7.59 (d, 1H, J=1.8 Hz), 7.42-7.37 (m, 3H), 7.31-7.27 (m, 3H), 7.01 (d, 1H, J=8.4 Hz), 4.27 (d, 2H, J=7.1 Hz), 4.19 (t, 1H, J=7.0 Hz), 3.26-3.21 (m, 2H), 2.72 (t, 2H, J=6.8 Hz). HRMS: found $[M+H]^+$ 508.1700. $C_{30}H_{26}N_3NaO_5^+$ requires 508.1872.

4-[5-(N-biotinyl-2-Aminoethyl)-2-hydroxyphenylazo]-benzoic acid (12)

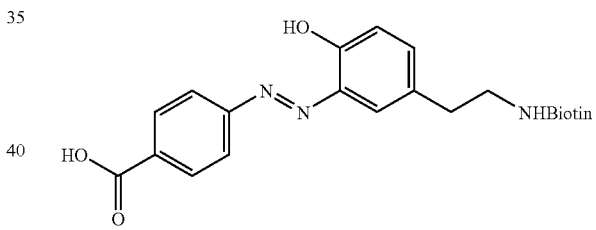

To 2-chlorotrityl resin (186 mg, 0.26 mmol) was added DCM (2 ml), 4-[5-(N-fluorenyloxycarbonyl-2-Aminoethyl)-2-hydroxyphenylazo]-benzoic acid (130 mg, 0.26 mmol) and DIEA (175 μl, 1.0 mmol). The mixture was gently shaken overnight at room temperature. Dry methanol (0.2 ml) was added to cap any unreacted resin (10 min). The resin was dried, and the loading efficiency was determined to be 0.85 mmol/g. The resin was swelled with dry DMF (2 ml) for 30 minutes, drained and treated with a 20% solution of piperidine in DMF (2 ml) for 30 minutes. The resin was drained and washed with DMF (5×5 ml) to remove residual traced of piperidine. To the resulting resin was added dry DMF (2 ml), biotin (73.3 mg, 0.30 mmol), PYBOP (156.1 mg, 0.30 mmol) and DIEA (104.5 μl, 0.60 mmol), and the resin was gently shaken at room temperature overnight. The resulting resin was drained, washed with DMF (3×3 ml), DCM (3×3 ml) and hexanes (3×3 ml) and dried in vacuo. Cleavage of the resin was performed using a 10% solution of TFA in DCM (10×2 minutes each). The organic fractions were combined, concentrated in vacuo, and dried via azeotrope with toluene to afford the desired 4-[5-(N-biotinyl-2-Aminoethyl)-2-hydroxyphenylazo]-benzoic acid (2) as an orange solid (65 mg, 50% from the benzoic acid).

4-[5-(N-biotinyl-2-Aminoethyl)-2-hydroxyphenylazo]-benzoicacid-(N'-hydroxy-3-sulfosuccinimide) ester (14)

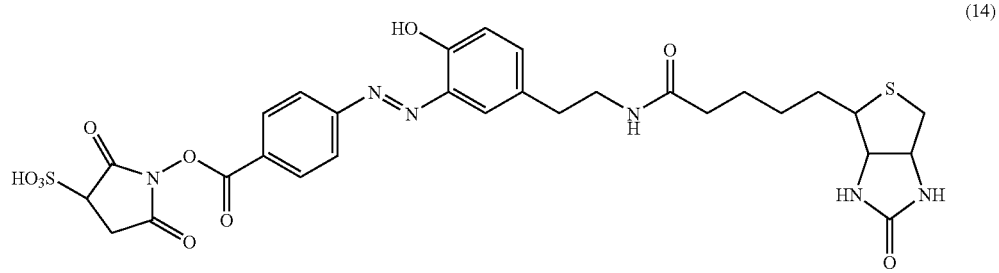

(14)

To a solution of (12) (65 mg, 0.14 mmol) in dry DMF (1 ml) was added N-hydroxysulfosuccinimide Sodium salt (43.4 mg, 0.20 mmol) and DIC (35.8 µl, 0.18 mmol), and the resulting mixture was stirred overnight at room temperature after which time it became a solution. LC-MS analysis indicated the starting material (12) had been consumed. The solution was concentrated in vacuo and purified by hplc to provide 4-[5-(N-biotinyl-2-Aminoethyl)-2-hydroxyphenylazo]-benzoicacid-(N'-hydroxy-3-sulfosuccinimide) ester (14) as an orange solid (67.1 mg, 77%).

This example shows the synthesis of another cleavable linker which can be used with biotin as an affinity tag and NHS-ester reactive group. The NHS ester preferably carries a solubility enhancing group such as sulfate. As described above, a variety of reactive groups are useful in the present cleavable linker system. In fact the intermediate

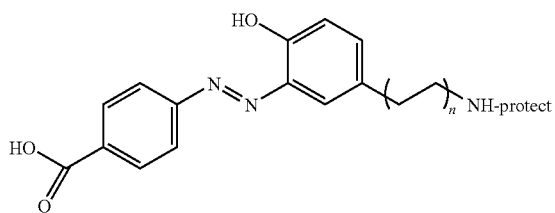

may be used to produce a cleavable linker with only the addition of an affinity tag in applications where the reactive group is a free acid. The amine terminus is protected with a known protective group such as Fmoc, and "n" may be from 0 to 5. That is, the linker retains the benzoic acid functionality. Free acid reactive groups are useful in binding to amine groups or the formation of esters when detecting or analyzing alcohols. One may also use as a reactive group 1-ethyl-3-[3-dimethylaminopropyl]carbodiimide hydrochloride (EDC or EDAC). EDC is a zero-length crosslinking agent used to couple carboxyl groups to primary amines. EDC reacts with a carboxyl to form an amine-reactive O-acylisourea intermediate. If this intermediate does not encounter an amine, it will hydrolyze and regenerate the carboxyl group. In the presence of N-hydroxysulfosuccinimide (Sulfo-NHS), EDC can be used to convert carboxyl groups to amine-reactive Sulfo-NHS esters. This is accomplished by mixing the EDC with a carboxyl containing molecule and adding Sulfo-NHS. The reactive group in this application would be used with a mixture of peptides and acids. Acid chloride cross linking agents are described in U.S. Pat. No. 6,303,150 to Perrier, et al., issued Oct. 16, 2001, entitled "Method for producing nanocapsules with crosslinked protein-based walls nanocapsules thereby obtained and cosmetic, pharmaceutical and food compositions using same." As described there, the cross-linking agent (reactive group) may be an acid dichloride, an acid anhydride or a dibasic or polybasic carboxylic acid. According to a preferred characteristic, the crosslinking agent is selected from terephthaloyl chloride, phthaloyl chloride, sebacoyl chloride, succinoyl chloride, the chloride of a tricarboxylic acid such as citric acid, or an acid anhydride such as succinic anhydride. One may also use nitrophenolic esters as reactive groups. This method comprises converting a carboxyl reactive group to a highly active ester group, and then reacting this ester to an amino group of the biologically active protein by e.g. the carbodiimide method, so that the linker and the biologically active protein are bonded by an amide linkage. The active ester includes, for example, a p-nitrophenyl ester, a 1,3,5-trichlorophenyl ester, a pentafluorophenyl ester, a 2,4-dinitrophenyl ester, an N-hydroxysuccinimide ester, an N-hydroxypyridine ester, an N-hydroxy-5-norbornen-2,3-dicarboxylic acid imide ester, a 8-hydroxyquinoline ester, and a 2-hydroxypyridine ester.

Isothiocyanate may be used as a reactive group to link to the carboxy terminus of peptides, as described in U.S. Pat. No. 5,968,834, "Method of carboxy terminal protein or peptide sequencing, issued Oct. 19, 1999.

Another reactive group is p-Diazobenzenesulfonic Acid. The use of this group is described in Kasai et al., "Chemical Modification of Tyrosine Residues in Ribonuclease T1 with N-Acetylimidazole and p-Diazobenzenesulfonic Acid," J. Biochem, 1977, Vol. 81, No. 6 1751-1758. As described there, three to four tyrosine residues in the enzyme Ribonuclease T1 were acetylated with N-acetylimidazole fairly readily at pH 7.5 without extensive loss of activity toward RNA. Of these, two residues appeared to be acetylated most easily. In the presence of phosphate anion, however, the reactivity of N-acetylimidazole was significantly lowered. Under the reaction conditions used, no acetylation took place in 0.2 m phosphate buffer. On the other hand, one to two tyrosine residues were modified with p-diazobenzenesulfonic acid in 0.2 m phosphate buffer, pH 7.0, without much loss of activity.

Example 4

Synthesis and Testing of Compounds where X=S, N or O and Y and Z are Hydroxyl Carboxy, Keto or Lower Alkyl As can be seen from the syntheses described above, different starting materials may be used in the procedures described in the Examples section above. The synthesis of the diazoaryl linker in FIG. 2 may be varied, for example, as described in U.S. Pat. No. 6,645,909 to Fujita, et al., issued Nov. 11, 2003, entitled "Process for azo coupling reaction using diazonium salt and coupler having releasing group, and recording material containing the coupler," and U.S. Pat. No. 5,539,088 to Schumacher, et al., issued Jul. 23, 1996, entitled "Water-soluble azo compounds, containing a diazo component with a heterocyclic moiety, and a coupling component with a fibre-reactive group, suitable as dyestuffs." Appropriate protective groups are added, and an activity based probe or other reactive group is installed as shown in FIG. 3. In order to test a modified probe, one reacts the molecule with a mixture containing the analyte to be bound to form a complex; passes the complex over an affinity support having a binding partner for the affinity tag, elutes the mixture, and cleaves the linkage with a mild reducing agent such as thionate for cleaving the N=N linkage. In passing the reducing agent over the support, the analyte should be freed from the support. The analyte, typically a protein, is identified as shown in connection with Table 2.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but which would be understood by workers in the field Such patents or publications are hereby incorporated by reference to the same extent as if each was specifically and individually incorporated by reference, as needed for the purpose of describing and enabling the method or material referred to.

REFERENCES

1. Leitner, A.; Lindner, W. J. Chromatogr. B 2004, 813, 1-26.
2. Zhang, H.; Yan, W.; Aebersold, R. Curr. Opin. Chem. Biol. 2004, 8, 66-75.
3. Tao, W. A.; Aebersold, R. Curr. Opin. Biotechnol. 2003, 14, 110-118.
4. Speers, A. E.; Cravatt, B. F. ChemBioChem 2004, 5, 41-47.
5. Verhelst, S. H. L.; Bogyo, M. QSAR Comb. Sci. 2005, 24, 261-269.
6. Schmidinger, H.; Hermetter, A.; Birner-Gruenberger, R. Amino Acids 2006, 30, 333-350.
7. Fauq, A. H.; Kache, R.; Kahn, M. A.; Vega, I. E. Bioconjugate Chem. 2006, 17, 248-254.

What is claimed is:

1. A compound for labeling and immobilizing a target protein, of the formula

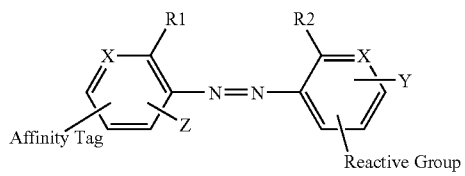

where
R1 and R2 are independently H, or hydroxyl, provided that at least one of R1 or R2 is hydroxyl;
X is independently one of CH, or N;
Y and Z are independently H, hydroxyl, carboxy, keto, or lower alkyl;
"Affinity Tag" represents a chemical moiety having a molecular weight of less than about 5,000 Daltons which has a specific binding partner; and
"Reactive Group" represents an affinity based probe which binds to a protein at a defined site and reacts with it.

2. The compound of claim 1 where the affinity tag is selected from the group consisting of biotin, Brilliant Blue FCF (BB FCF), azorubine, phytoestrogen, digoxigenin, nickel, cobalt, zinc, and a hapten to an antibody.

3. The compound of claim 2 where the affinity tag is biotin.

4. The compound of claim 3 where the affinity tag is of the formula:

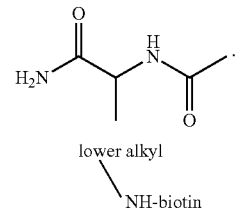

5. The compound of claim 1 where the reactive group is selected from the group consisting of mercaptoaminomonocarboxylic acids, diaminomonocarboxylic acids, monoaminodicarboxylic acids, metal chelates, semicarbazones, epoxy succinyl, acyl oxy, and peptidyl phenyl phosphonate, N hydroxyl succinimide, carboxylic acid, acid chloride, nitrophenolic ester, EDC ("1-ethyl-3-[3-dimethylaminopropyl] carbodiimide hydrochloride") and p-diazobenzenesulfonic acid.

6. The compound of claim 1 where the Reactive Group is an affinity based probe comprising a derivatized peptide reactive with a protease.

7. The compound of claim 6 where the Reactive Group comprises AOMK ("acyloxymethyl ketone") or epoxide.

8. The compound of claim 1 where the Reactive Group is a derivatized peptide having a reactive group selected from the group consisting of an AOMK group, a phenyl phosphonate, and an epoxy succinyl group, and said peptide has between 2 and 5 amino acid units.

9. The compound of claim 1 where the diazo bond is in the m position relative to the Reactive Group.

10. The compound of claim 9 where X=C.

11. The compound of claim 1 further comprising a label bound to the Reactive Group.

12. The compound of claim 11 where the label is a fluorescent label.

13. A compound useful in synthesizing a cleavable linker, of the formula:

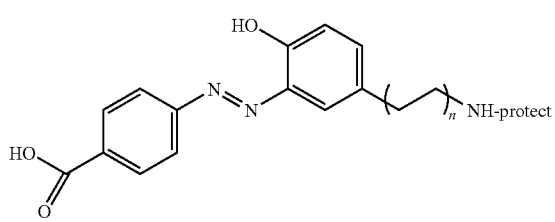

where n represents the number of atoms in the lower alky linking group and may be between 0 and 5, and "protect" represents an amine protective group Fmoc fluorenylmethoxycarbonyl-, Boc tert-butyoxycarbonyl-, or Cbz carbobenzyloxy-.

14. A compound according to claim 1 of the formula:

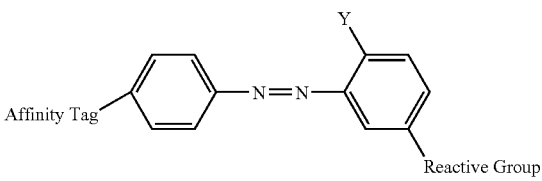

and Reactive Group is an affinity based probe which is a derivatized peptide reactive with a protease and comprising AOMK or epoxide.

* * * * *